United States Patent [19]

Van Lookeren

[11] Patent Number: 5,055,571

[45] Date of Patent: Oct. 8, 1991

[54] METHOD OF PURIFYING CRUDE POLYOL FATTY ACID POLYESTERS

[75] Inventor: Gerard J. Van Lookeren, Sonderborg, Denmark

[73] Assignee: Van den Bergh Foods Co., Division of Conopco Inc., Lisle, Ill.

[21] Appl. No.: 279,688

[22] Filed: Dec. 5, 1988

[30] Foreign Application Priority Data

Dec. 4, 1987 [GB] United Kingdom ............... 8728385

[51] Int. Cl.$^5$ ..................... C07H 1/00; C08B 37/00
[52] U.S. Cl. ..................... 536/124; 536/127; 536/120; 536/119; 536/115
[58] Field of Search ............... 536/124, 127, 119, 115, 536/120

[56] References Cited

U.S. PATENT DOCUMENTS

| | | | |
|---|---|---|---|
| 3,963,699 | 6/1976 | Rizzi et al. | 536/119 |
| 4,334,061 | 6/1982 | Bossier | 536/119 |
| 4,517,360 | 5/1985 | Volpenhein | 536/124 |
| 4,518,772 | 5/1985 | Volpenhein | 536/124 |
| 4,611,055 | 9/1986 | Yamamoto et al. | 536/127 |

FOREIGN PATENT DOCUMENTS 0349221  1/1990  European Pat. Off. .

*Primary Examiner*—Ronald W. Griffin
*Assistant Examiner*—Everett White
*Attorney, Agent, or Firm*—Gerard J. McGowan, Jr.

[57] ABSTRACT

The present invention pertains to a method of purifying crude polyol fatty acid polyesters, in particular sugar polyesters, comprising, preferably more than one, alkaline washing treatments at pH of at least 12.5, optionally in combination with water and/or acid washing treatments and further conventional refining steps. By this method better color-removal and stability against high-temperature discoloring is achieved.

18 Claims, No Drawings

METHOD OF PURIFYING CRUDE POLYOL FATTY ACID POLYESTERS

The present invention relates to a method of purifying crude polyol fatty acid polyesters, and particularly, although not exclusively, crude sugar gatty acid polyesters.

Polyol fatty acid polyesters and in particular, the sugar fatty acid polyesters, such as e.g. the sucrose fatty acid polyesters, are known as suitable low-calorie fat-replacers in edible products. Substantially indigestible for human beings they have physical and organoleptic properties very similar to triglyceride oils and fats conventionally used in edible products. In addition, polyol fatty acid polyesters are reported to have use as pharmaceutical agents e.g. in view of their ability to take up fat-soluble substances, such as in particular cholesterol, in the gastro-intestinal tract, and subsequently remove these substances from the human body.

In this specification the term "polyol" is intended to include any aliphatic or aromatic compound which comprises at least four free hydroxyl groups. Such polyols in particular include the group of sugar polyols, which comprises the sugars, i.e. the mono-, di- and polysaccharides, the corresponding sugar alcohols and the derivatives thereof having at least four free hydroxyl groups. Examples of sugar polyols include glucose, mannose, galactose, xylose, fructose, sorbose, tagatose, ribulose, xylulose, maltose, lactose, cellobiose, raffinose, sucrose, erythritol, mannitol, lactitol, sorbitol, xylitol and α-methylglucoside. A generally used sugar polyol is sucrose.

The term "polyol fatty acid polyester" is intended to include any such polyesters or mixtures thereof of which, on an average, more than 70% of the polyol hydroxyl groups have been esterified with fatty acids.

The term "fatty acid" refers to $C_8-C_{24}$ fatty acids which may be saturated or unsaturated, and may have straight or branched alkyl chains.

In general polyol fatty acid polyesters are synthesized by processes in which a polyol, such as a mono- or disaccharide, is reacted with a fatty acid lower alkylester, frequently the fatty acid methylester, in the presence of a transesterification catalyst, such as e.g. an alkali metal hydroxide or carbonate. In a first stage a polyol fatty acid mono- or oligoester is formed, which in a second stage is further reacted with the fatty acid lower alkylester to form polyol fatty acid polyesters of the desired degree of esterification. It is also possible to combine the two stages of the reaction into a single step.

Processes of this type are described in e.g. the U.S. Pat. specifications Nos. 3,963,699, 4,517,360, and 4,518,772.

The crude polyol fatty acid polyester reaction products resulting from conventional syntheses contain in addition to the desired polyesters, components such as fatty acid, soaps, excess fatty acid lower alkylesters and polyol fatty acid oligoesters. Also, due to the relatively high temperatures at which conventional syntheses are carried out, often by-products are formed which may be undesirable in view of their chemical characteristics, such as in particular discolouring properties. In general it is therefore necessary to further purify or refine the crude polyol fatty acid polyester reaction products resulting from such conventional syntheses.

For the purposes of this specification crude polyol fatty acid polyesters are defined as unrefined or incompletely refined reaction products of processes for the synthesis of polyol fatty acid polyesters. Such crude compositions in general contain of from 10 to 95% by weight of polyol fatty acid polyesters.

Conventional purification methods include washing with water, extraction with organic solvents, and/or salting-out treatments. In the U.S. Pat. specification No. 4,334,061 there is described a process for the preparation of sucrose fatty acid polyesters, in which the reaction product is washed using an aqueous alkaline solution of pH 7-12 in the presence of a polar organic solvent.

It has been found that such conventional purification methods are not always fully reliable, in particular, with respect to their colour-removing ability. If a full refining process is used including e.g. conventional steam-stripping or deodorising steps, discolouring of the polyesters may again occur, even where initially an almost de-coloured product resulted from the conventional purification step. Moreover, the use of organic solvents is from a technical and economic point of view undesirable.

Accordingly, there is still a need for improved methods of purifying crude polyol fatty acid polyesters which do not suffer from the drawbacks of prior art methods, and in which the use of organic solvents is avoided.

The present invention now provides a method of purifying crude polyol fatty acid polyesters comprising an alkaline washing step in which said polyesters are submitted to a treatment with a suitable amount of an aqueous alkaline solution having a pH of at least 12.5.

Somewhat dependent of the desired or necessary degree of purification and of the further purification or refining steps that may be employed, a suitable amount of the aqueous alkaline solution varies between 0.1 to 15% by weight of the crude polyol fatty acid polyesters. In particular, amounts in the range of from 2 to 12% by weight, preferably of from 5 to 10% by weight, have been found suitable.

Conventional alkaline materials can be used to provide aqueous alkaline solutions having a pH of at least 12.5. Suitable such materials include alkali metal and earth alkali metal hydroxides. Preferably, sodium hydroxide is used. The aqueous alkaline solution preferably has a pH of at least 13 corresponding to concentrations of the alkaline material of at least 0.1 N. Preferably, 1 to 9 N NaOH solutions are used. Most preferably, aqueous NaOH solutions having a strength of 2 to 6 N are applied.

The alkaline washing step in accordance with the present invention is preferably carried out at elevated temperature, in particular at a temperature of from 40 to 110° C., and most preferably at a temperature of from 60° to 100° C.

In general the crude polyesters and the aqueous alkaline solution are agitated to ensure sufficient contact between the components of the polyester mixture and the washing solution. In batch-wise operation contacting times of less than one hour are normally sufficient. In particular, contacting times lie within the range of 1 to 30 minutes, 3 to 15 minutes being preferred. In a continuous operation, e.g. where the aqueous alkaline solution is in-line dosed to the crude polyester and the mixture is subsequently centrifuged, contact times in general are less than about 3 minutes, in particular, less than about 1 minute, and can be as short as 5 to 30 seconds.

Purification results may be further advantageously affected when a sequence of two or more washing steps with aqueous alkaline solutions in accordance with the invention are used.

Dependent of the amount of soap present in the crude polyesters it may be of further advantage to have the alkaline washing step be preceded by a reduction of the soap level. Suitably, such a reduction of the soap level is effectuated by way of centrifuging or filtrating off crystallised soap, and/or one or more preceding washing treatments with aqueous near-neutral solutions having a pH in the range of 4–9, in particular of 5–8. The aqueous near-neutral solution may further advantageously comprise an electrolyte, such as NaCl, in an amount of up to 2%, preferably in the range of from 0.3–1.5% by weight of the crude polyesters.

In general the aqueous near-neutral washing solution is used in an amount of up to 50% by weight of the crude polyesters. Amounts of up to 15%, particularly, in the range of from 5 to 10% by weight are preferred.

If a sequence of two or more alkaline washing steps is applied, also the first alkaline washing step can be suitably used to achieve said initial reduction of the soap level.

Although the polyester phase and the water phase in the alkaline and the optional near-neutral washing steps can be separated by gravity settling only, separation by centrifuging is preferred. In general the above described washing steps in accordance with the invention will be part of a full refining process. Such a full refining process may and preferably does include a further acid washing step in which the polyol fatty acid polyesters resulting after the alkaline washing step are treated with an aqueous solution of an acid such as in particular phosphoric acid or citric acid. Both the alkaline and the optional acid washing steps may be followed by further washing treatments with aqueous near-neutral solutions, and/or drying steps.

Subsequent to the washing treatments the polyol fatty acid polyesters can be further purified using conventional refining techniques such as bleaching with activated carbon and/or bleaching earth, distilling at a temperature of about 170° to 210° C., and/or deodorising, such as steam-stripping, at a temperature of 180° to 260° C., preferably 190° to 220° C.

By the method of the invention refined polyol fatty acid polyesters are obtained which are de-coloured to a high degree. The method of the invention can also advantageously be used to upgrade polyol fatty acid polyesters that have discoloured during high temperature processing. Moreover, the keepability of the polyesters purified according to the present invention is generally improved. The method of the invention has the further advantage that the use of organic solvents can be avoided.

Although the method according to the invention is suitable for purifying crude products of the general group of polyol fatty acid polyesters as defined hereinbefore, it is particularly suitable for purifying crude products comprising polyol fatty acid polyesters of which, on an average, more than 80%, or even 90% of the hydroxyl groups of the polyol have been esterified with fatty acids. In particular, such polyesters derived from the sugar polyols selected from the group of disaccharides or the alcohol derivatives thereof, such as sucrose, and esterified to over 95% fatty acid substitution, are suitable purified by the method in accordance with the present invention.

The invention is now further illustrated with reference to the following examples, percentages being by weight unless indicated otherwise.

Comparative example A illustrates purification method in accordance with the procedure disclosed in U.S. Pat. No. 4,334,061, further examples are illustrations of the purification method in accordance with the present invention.

COMPARATIVE EXAMPLE A

A crude sucrose fatty acid polyester mixture (polyester fatty acid residues derived from distilled soybean methyl esters) comprising about 12% soap and 30 fatty acid methyl esters was subjected to a washing treatment according to a conventional method of purification. The crude mixture was heated to 80° C. in a stirred vessel, and 33% of an isopropyl alcohol-water solution (17% isopropyl alcohol, 2% Soda, 81% $H_2O$) was added in. After 5 minutes of mixing and 30 minutes of settling the water phase was separated. This treatment was repeated twice, after which 2% acetic acid was added and two water washings (30% $H_2O$) were applied. After consecutive drying and filtration this resulted in a mixture of about 65% sucrose fatty acid polyester and 35% fatty acid methylester with a colour of 8 Yellow+0.8 Red in a Lovibond 5¼" cell. After subsequent bleaching and deodorizing the purified sucrose fatty acid polyester showed a colour of 22 Yellow+2.2 Red. A second batch (polyester fatty acid residues now derived from non-distilled soybean methyl esters) was subjected to the same washing treatment resulting after drying in a colour of 52 Yellow+5.3 Red and after bleaching and deodorizing in a colour of 50 Yellow+7.6 Red.

EXAMPLE 1

The same crude sucrose fatty acid polyester mixtures of example A were used in a washing treatment in accordance with the method of the present invention. The crude material was subjected to water and alkaline washings at 80° C. 10% of an aqueous 10% NaCl solution was added to the crude sucrose fatty acid polyesters. After 15 min. of mixing the coloured water-soap phase was separated with a centrifuge. Then 5% of a 4 N NaOH solution was added followed by 15 min. mixing and centrifugal separation of the coloured water-soap phase. This alkaline washing was repeated. After drying sucrose fatty acid polyester / fatty acid methylester mixtures were obtained having colour characteristics of 8 Yellow+0.8 Red (using distilled methyl ester) and 28 Yellow+2.8 Red (using non-distilled methyl ester). After subsequent bleaching and deodorizing the two sucrose fatty acid polyester batches were characterized by colours of 16 Yellow+0.6 Red and 40 Yellow+4.0 Red.

Comparison of the results of Example A and Example 1 clearly shows that by the purification method in accordance with the present invention the use of organic solvents can be avoided while achieving equal or better purification results.

EXAMPLE 2

Four purification experiments were compared, (a), (b) and (c) being in accordance with the present invention, whereas experiment (d) did not include the alkaline washing treatment in accordance with the invention.

(a) A crude sucrose fatty acid polyester mixture (polyester fatty acid residues derived from nondistilled soybean methyl esters) comprising about 40% of fatty acid methylester and about 10% of soap was heated up to 80° C. in a stirred vessel, 10% of an aqueous 10% NaCl solution was added and after 15 minutes the soap phase was settled with a centrifuge. The sucrose fatty acid polyester / fatty acid methylester-phase was washed twice with 5% of 4 N NaOH solution at 80° C. The soap content at this stage was 400 ppm. To remove the residual soap, 2% of citric acid was added and after strong agitation the sucrose fatty acid polyester / fatty acid methylester mixture was washed pH neutral with water and dried. By measuring the soap content with atomic adsorption spectroscopy analyzing for sodium and potassium, it was found that the levels of both alkali metals were below 0.1 ppm.

The colour in the Lovibond 5¼" cell after drying was 30 Yellow+3.0 Red. After bleaching and deodorizing at 190° C. the final colour was 30 Yellow+3.2 Red in the 5¼" cell.

(b) The refining procedure under (a) without the initial 10% NaCl washing resulted in a colour of 30 Yellow+3.0 Red after drying and a colour of 30 Yellow 3.1 Red after bleaching and deodorizing.

(c) The refining procedure under (b) without the second lye washing resulted in a colour of 40 Yellow+3.8 Red after drying and a colour of 40 Yellow+3.5 Red after bleaching and deodorizing.

(d) The refining procedure under (a) without any lye washing, but extended by, after the initial 10% NaCl washing, two further washings with 5% of 10% NaCl solutions and five washings with 10% of water, resulted in a colour of 40 Yellow+5.6 Red after drying and 60 Yellow +9.0 Red after bleaching and deodorizing.

The results of the experiments (a)-(c) over experiment (d) clearly show the advantagous effects by the alkaline treatment in accordance with the method on the colour characteristics of the refined polyol fatty acid polyesters.

EXAMPLE 3

A batch of sucrose fatty acid polyesters (polyester fatty acid residues derived from a mixed blend of 53% Palm Kernel and 47% Palm oil) had darkened during deodorizing at 190° C. to a colour of 31 Yellow+5.2 Red (Lovibond 2"cell), while the colour before deodorizing was 2.0 Yellow+0.2 Red in the Lovibond 5¼" cell.

The darkened sucrose fatty acid polyester mixture, consisting of 95% sucrose fatty acid polyesters, was subjected to an alkaline washing with 5% aqueous solution of 4 N sodium hydroxide. After consecutive citric acid washing, bleaching and deodorizing the final colour was 11.2 Yellow+2.0 Red in the 5¼" cell and 2.9 Yellow+0.8 Red in the Lovibond 2" cell.

EXAMPLE 4

A crude sucrose fatty acid polyester (polyester fatty acid residues derived from a mixed blend of 45% of touch-hardened and 55% of fully hardened soybean oil) was subjected to a purification process as described in Example 2 (b). The resulting colour characteristics after bleaching and deodorizing were 20 Yellow+2.0 Red in the 5¼" cell.

What is claimed is:

1. A process of purifying crude polyol fatty acid polyesters comprising conducting an alkaline washing step by submitting said polyesters to a treatment with a suitable amount of an aqueous alkaline solution having a pH of at least 13.

2. The process according to claim 1 in which the aqueous alkaline solution is applied in an amount of 2 to 12% by weight of said crude polyesters.

3. The process according to claim 1 in which said alkaline washing step is carried out at a temperature of from 40° to 110° C.

4. The process according to claim 1 in which a sequence of two or mroe of said alkaline washing steps is used.

5. The process according to claim 1 in which said alkaline washing step is preceded by one or more washing steps with an aqueous solution having a pH within the range of from 4 to 9.

6. The process according to claim 5 in which said aqueous solution is applied in an amount of from 5 to 10% by weight of said crude polyesters, and comprises from 0 to 2%, calculated by weight of said crude polyesters, of an electrolyte.

7. The process according to claim 1 in which said alkaline washing step is followed by one or more washing steps including a treatment with an aqueous solution of an acid.

8. The process according to claim 1 which further comprises a bleaching and deodorizing step.

9. The process according to claim 1 in which said crude polyesters comprise polyol fatty acid polyester derived from sucrose esterified to over 95% fatty acid substitution.

10. A process of purifying crude polyol fatty acid polyesters comprising conducting an alkaline washing step in the absence of an organic solvent by submitting said polyesters to a treatment with a suitable amount of an aqueous alkaline solution having a pH of at least 12.5.

11. The process according to claim 10 in which the aqueous alkaline solutin is applied in an amount of 2 to 12% by weight of said crude polyesters.

12. The process according to claim 10 in which said alkaline washing step is carried out at a temperature of from 40° to 110° C.

13. The process according to claim 10 in which a sequence of two or more of said alkaline washing steps is used.

14. The process according to claim 10 in which said alkaline washing step is preceded by one or more washing steps with an aqueous near-neutral solution.

15. The process according to claim 14 in which said aqueous near-neutral solution is applied in an amount of from 5 to 10% by weight of said crude polyesters, and comprises from 0 to 2%, calculated by weight of said crude polyesters, of an electrolyte.

16. The process according to claim 10 in which said alkaline washing step is followed by one or more washing steps including a treatment with an aqueous solution of an acid.

17. The process according to claim 10 which further comprises bleaching and deodorizing.

18. The process according to claim 10 in which said crude polyesters comprise polyol fatty acid polyester derived from sucrose esterified to over 95% fatty acid substitution.

* * * * *